United States Patent
McGregor et al.

(10) Patent No.: US 6,713,083 B1
(45) Date of Patent: Mar. 30, 2004

(54) COATED BIOABSORBABLE BEADS FOR WOUND TREATMENT

(75) Inventors: James McGregor, Glasgow (GB); Paul W. Watt, Steeton (GB)

(73) Assignee: Johnson & Johnson Medical, Ltd. (GB)

( * ) Notice: Subject to any disclaimer, the term of this patent is extended or adjusted under 35 U.S.C. 154(b) by 191 days.

(21) Appl. No.: 09/142,814

(22) PCT Filed: Mar. 7, 1997

(86) PCT No.: PCT/GB97/00638

§ 371 (c)(1), (2), (4) Date: May 21, 1999

(87) PCT Pub. No.: WO97/34645

PCT Pub. Date: Sep. 25, 1997

(30) Foreign Application Priority Data

Mar. 15, 1996 (GB) .............................................. 9605422

(51) Int. Cl.[7] .................................................. A61K 9/70
(52) U.S. Cl. ...................... 424/443; 424/443; 424/444; 424/445; 424/447; 428/408; 530/534; 530/536
(58) Field of Search .................................. 424/443, 444, 424/445, 447; 428/408; 530/534, 536

(56) References Cited

U.S. PATENT DOCUMENTS

| 4,280,954 A | 7/1981 | Yannas et al. |
| 4,347,234 A | 8/1982 | Wahlig et al. |
| 4,453,939 A | 6/1984 | Zimmerman et al. |
| 4,713,076 A | 12/1987 | Draenert |
| 4,818,542 A | 4/1989 | DeLuca et al. |
| 4,837,285 A | * 6/1989 | Berg et al. ................... 530/356 |
| 4,970,298 A | * 11/1990 | Silver et al. ................ 530/356 |

FOREIGN PATENT DOCUMENTS

| EP | A-0159036 | 10/1984 |
| EP | WO 9106286 | 5/1991 |
| EP | 0562864 A1 | 9/1993 |
| EP | 648480 | 4/1995 |
| GB | 2280372 A | 2/1995 |
| GB | A-2281861 | 3/1995 |

OTHER PUBLICATIONS

International Preliminary Examination Report Appliction No. PCT/GB97/00638, Jun. 25, 1997.

* cited by examiner

Primary Examiner—Russell Travers
Assistant Examiner—S Sharareh
(74) Attorney, Agent, or Firm—Theodore Shatynski

(57) ABSTRACT

The invention provides a material for use in a wound dressing or wound implant, the material comprising a plurality of beads, wherein each bead comprises a porous core of a first bioabsorbable material and a substantially nonporous layer of a second bioabsorbable material around the core. The porous core is preferably a sponge formed by freeze-drying a liquid suspension of the first bioabsorbable material. The preferred diameter of the beads is 0.1–4.0 mm, and the beads are preferably dispersed in a liquid or solid matrix. The invention also provides a method of making beads for use in the materials of the invention.

10 Claims, 5 Drawing Sheets

COATED BIOABSORBABLE BEADS FOR WOUND TREATMENT

CROSS-REFERENCE TO RELATED APPLICATIONS

This application is based upon PCT Application Serial No. PCT/GB97/00638, filed Mar. 7, 1997, which claims priority from European Patent Application Serial No. 9605422.6, filed on Mar. 15, 1996.

The present invention relates to coated bioabsorbable beads for use in a wound dressing or wound implant.

It is known to use collagen-based bioabsorbable beads for augmenting soft tissue in wound dressings and wound implants. U.S Pat. No 4,837,285 describes the use of collagen matrix beads, the beads being formed from a sponge of resorbable collagen. The beads have an average pore size of from 50 to 350 $\mu$m, with the collagen comprising from 1 to 30% by volume of the beads. The size of the beads is preferably from 0.1 to 4 mm diameter. The collagen matrix is sufficiently open to simulate cellular ingrowth therethrough, and yet sufficiently stiff and non-compressible to fill and protect a wound, and sufficiently moisture and gas permeable to prevent liquid pooling on a wound and to permit sufficient oxygen diffusion for promoting wound healing.

EP-A-0648480 describes wound implant materials comprising a plurality of bioabsorbable microspheres bound together by a bioabsorbable matrix. The microspheres are preferably hollow microspheres or microcapsules bound together in a freeze-dried matrix. Preferably, at least 90% of the microspheres have diameters between 0.2 and 1.0 mm. The use of closely packed microspheres having controlled diameters is said to allow good control over the porosity of the implant material.

A need remains for improved materials for use in wound dressings and wound implants. Such a material should preferably be inexpensive and easy to manufacture in a range of wound treatment formats. The material should preferably be fully bioabsorbable and non-antigenic. The material should preferably allow precise control of wound healing kinetics so as to assist rapid wound healing with minimum scarring.

It is an object of the present invention to provide a material for use in a wound dressing or wound implant having the desirable properties listed above.

It is a further object of the present invention to provide a method of making bioabsorbable beads for use in a material for use in wound dressings or wound implants having the desirable properties listed above.

The present invention provides a material for use in a wound dressing or a wound implant. The material comprises a plurality of beads, wherein each bead comprises a porous core of a first bioabsorbable material and a substantially non-porous layer of a second bioabsorbable material around said core.

The first and second bioabsorbable materials may be any materials that are fully absorbable in the mammalian body. Such materials include synthetic bioabsorbable materials commonly used for surgical sutures, implants and the like, for example absorbable polymers and copolymers made from poly-glycolide, poly-lactide, $\epsilon$-caprolactone, p-dioxanone, trimethylene carbonate and dimethyl trimethylene carbonate monomers.

Preferably, the first and second bioabsorbable materials are biopolymer materials or chemically modified biopolymer materials. Such materials include polysaccharides such as oxidised regenerated cellulose, alginates, chitosan or naturally occurring gums such as guar gum, xanthan gum or the like. Suitable biopolymers also include glucosaminoglycans, such as hyaluronic acid, chondroitin sulphate, heparin and heparan sulphate. However, the preferred biopolymers are hyaluronic acid and its salts, and the structural proteins such as collagen, fibrin, laminin or fibronectin. More preferred is collagen, which encompasses all collagen types including type I collagen, type II collagen, atelocollagen, pepsin-solubilised collagen and gelatin. Fibrous, insoluble collagen is most preferred.

Collagen is preferred because of its low antigenicity, ready availability at moderate cost, and well-understood properties.

Preferably, the first bioabsorbable material consists essentially of collagen. More preferably, both the first and second bioabsorbable materials consist essentially of collagen.

The porous core of the first bioabsorbable material is preferably a bioabsorbable sponge, for example a product of freeze-drying (lyophilising) or solvent drying a frozen liquid dispersion of the biopolymer. Such sponges generally have irregular, interconnected pores. Preferably, the average pore diameter is in the range of 50 $\mu$m to 350 $\mu$m, which is thought to be the optimum size range for fibroblast ingrowth.

Preferably, the beads are substantially spherical. More preferably, the substantially spherical beads comprise a substantially spherical porous core enclosed in a substantially non-porous layer of substantially uniform thickness.

Preferably, the mean outside diameter of the beads in the range 0.1 to 4.0 mm. More preferably, the mean outside diameter of said beads is in the range 0.2 to 1.0 mm. Preferably, the layer of the second bioabsorbable material is of substantially uniform thickness. Preferably, the average thickness of said layer is in the range 0.01 mm to 1.0 mm, more preferably 0.02 mm to 0.1 mm. Preferably, said layer forms a substantially continuous coating over the core to substantially prevent cellular invasion of the core until the layer has fully degraded in the body.

The beads may also comprise an active therapeutic agent in the porous core and/or in the layer around the core. Preferred active therapeutic agents include growth factors such as TGF$\beta$, platelet derived growth factor (PDGF) or fibroblast growth factor (FGF) that can promote the ingrowth of wound healing cells. The beads are especially suitable for achieving slow, more especially phased release of active therapeutic agents at the wound site. Such agents can include antiseptics such as chlorhexidine or silver sulphadiazine, antibiotics such as a penicillins or a tetracyclins, steroids such as cortisone or prednisone, or non-steroidal anti-inflammatory drugs such as Ibuprofen, naproxen or acetaminophen. Phased release of the active therapeutic agents can be achieved by having different concentrations of one or more different active agents in the porous core and the outer layer of the bead, respectively.

In certain preferred embodiments the material according to the present invention is a fluid, gel or paste comprising the coated beads as described above dispersed in a pharmaceutically acceptable liquid or gel carrier. The carrier can be a non-toxic base for forming an ointment, gel or injectable fluid incorporating the coated beads. The carrier is preferably an aqueous carrier, and may also comprise a polyhydric alcohol such as propyleneglycol as a humectant, a pharmaceutically acceptable gelling agent such as gelatin, or hyaluronic acid and its salts. The carrier may include pharmaceutical active agents, including any one or more of the pharmaceutical active agents for the beads enumerated above.

In other preferred embodiments the material according to the present invention may be a solid wound implant material comprising a plurality of the coated beads bound together by a bioabsorbable matrix, as described and claimed in our pending European patent application EP-A-0648480, the entire contents of which are expressly incorporated herein by reference.

Preferably, the matrix is a solid bioabsorbable material, preferably formed by freeze-drying an aqueous dispersion of a bioabsorbable material that has been used to bind the coated beads.

Preferably, the coated beads make up at least 30%, more preferably at least 40%, and most preferably at least 50% of the volume of the material according to the present invention.

The present invention also provides a method of making bioabsorbable beads for use in wound dressings or implants, the method comprising: providing a dispersion of a first bioabsorbable material in a liquid solvent; generating droplets of the dispersion; freezing the droplets to form frozen droplets; freeze-drying or solvent drying the frozen droplets to form discrete porous cores of said first bioabsorbable material; and coating the porous cores with a substantially non-porous layer of a second bioabsorbable material.

The preferred compositions and dimensions of the bioabsorbable beads are as described above for the materials according to the present invention.

Preferably, the liquid solvent is an aqueous solvent. The dispersion may be a suspension or a solution, and preferably has a weight concentration of 0.01–5% w/v, more preferably 0.02%–2% w/v.

The droplets of the dispersion can be generated by methods conventionally known in the art, including spraying the dispersion through a suitable nozzle with or without application of an electric field, pulsing individual droplets from a capillary, or emulsifying the aqueous dispersion in a water-immiscible solvent such as a volatile hydrocarbon.

Once formed, the droplets are preferably immediately frozen, for example by spraying the droplets into liquid nitrogen. Emmulsified droplets are frozen by chilling the emulsion to a temperature below the freezing point of the dispersion but above the freezing point of the water-immiscible solvent, followed by filtering off the frozen droplets. The frozen droplets are then preferably sieved to isolate droplets having the desired size range. Broadly speaking, the porous cores formed by freeze-drying or solvent drying the frozen droplets will have approximately the same dimensions as the frozen droplets.

The frozen droplets are then freeze-dried or solvent dried. The freeze-drying is preferably carried out over a temperature range of −20° C. to ambient using conventional freeze-drying apparatus. The solvent drying is preferably carried out as described in U.S. Pat No. 3,157,524, the entire contents of which are expressly incorporated herein by reference. Briefly, the solvent drying is carried out by immersing the frozen droplets in a series of anhydrous isopropanol baths maintained at ambient temperature, followed by evaporation of residual isopropanol under vacuum.

Finally, the porous cores of bioabsorbable material formed in the above process steps are coated with a substantially non-porous layer of a second bioabsorbable second material. The coating is preferably carried by dipping the cores in a solution of the second bioabsorbable material, or by spray coating, followed by drying. The thickness of the coating layer will depend on the concentration and viscosity of the dipping solution, and on the number of dipping/spray coating operations carried out.

The finished coated beads, preferably comprise less than 10% water by weight, and are preferably then sterilized by gamma irradiation.

The coated beads having porous bioabsorbable cores obtained by the method of the present invention are especially useful for soft tissue filling in wound dressings and implants. This is because the interstices between the beads in the wound dressing or implant are rapidly invaded by wound healing cells, especially fibroblasts. However, the interiors of the beads themselves are not invaded until after the non-porous coating on the beads has been degraded by bioabsorbtion. This allows more accurate control over later stage wound healing, and hence permits reduction in scarring.

Specific embodiments of the present invention will now be described further, by way of example, with reference to the accompanying Figures, in which.

EXAMPLE 1

Preparation of Coated Beads

Coated beads for use in materials according to the present invention are prepared by a method according to the present invention, as follows. A solution of 1% chitosan in 1% acetic acid is pumped through a fine pipette tip using a peristaltic pump. The droplets thus formed are dropped into liquid nitrogen in a Dewar flask to form frozen droplets of the solution. The Dewar flask is shaken slight to ensure that the beads do not stick together before they are completely frozen. The frozen beads are collected and sieved to collect beads having diameters in the range 1 mm–2 mm.

The frozen droplets are then transferred to a freeze-dryer and lyophilized at −20° C. to about +20°. The freeze-dried beads are then coated by dipping them into a 10–20% w/v solution of a 1:1 polylactic acid/polyglycolic acid copolymer having molecular weight 50,000–75,000 (Sigma Chemical Co.) in chloroform at ambient temperature for about 10 seconds, followed by drying in a current of warm air.

Figure 1:
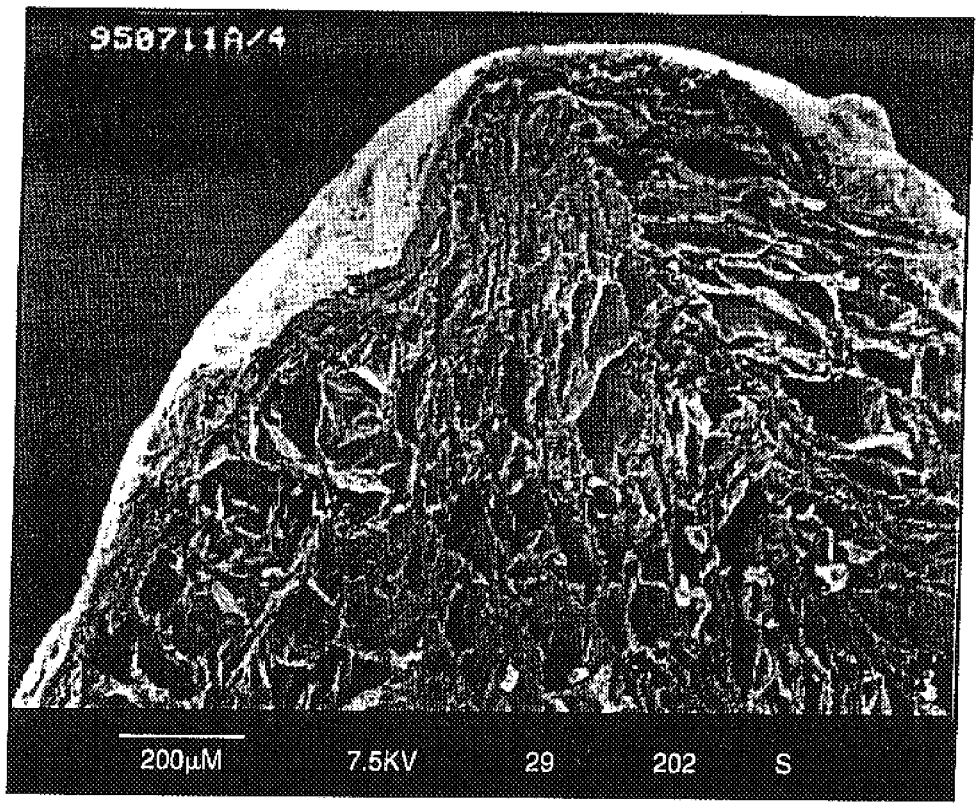
FIG. 1 shows a photomicrograph of part of a section through a coated bead obtained by the method of the present invention.
Figure 2:
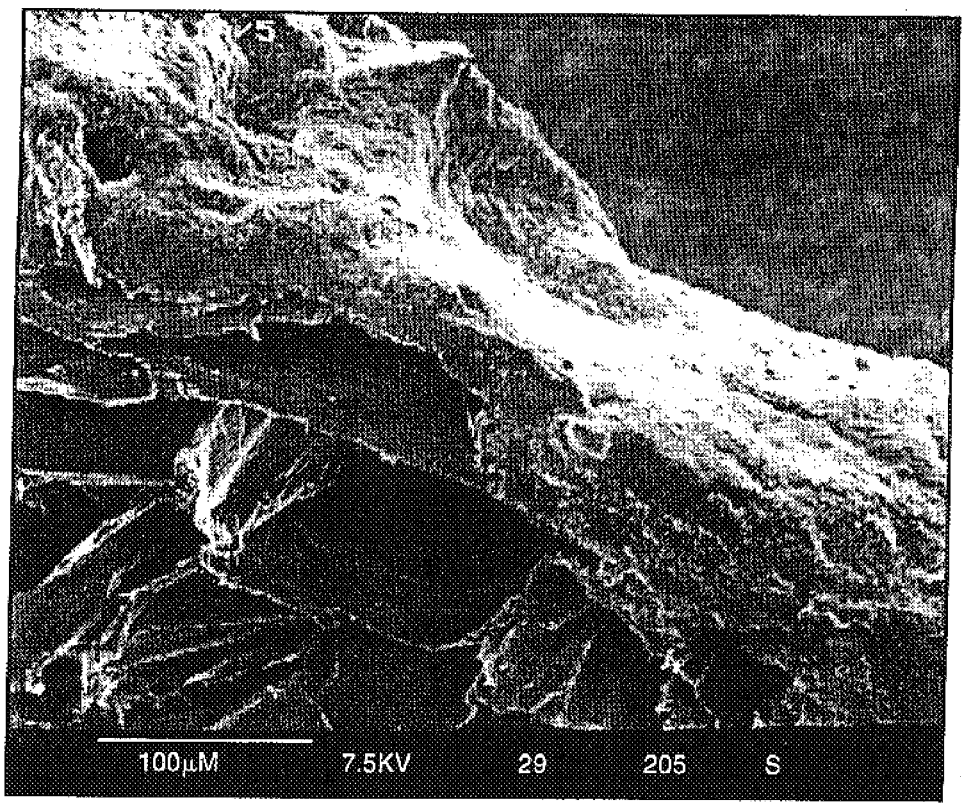
FIG. 2 shows a detail of part of the bead of FIG. 1 at higher magnification.
Figure 3:
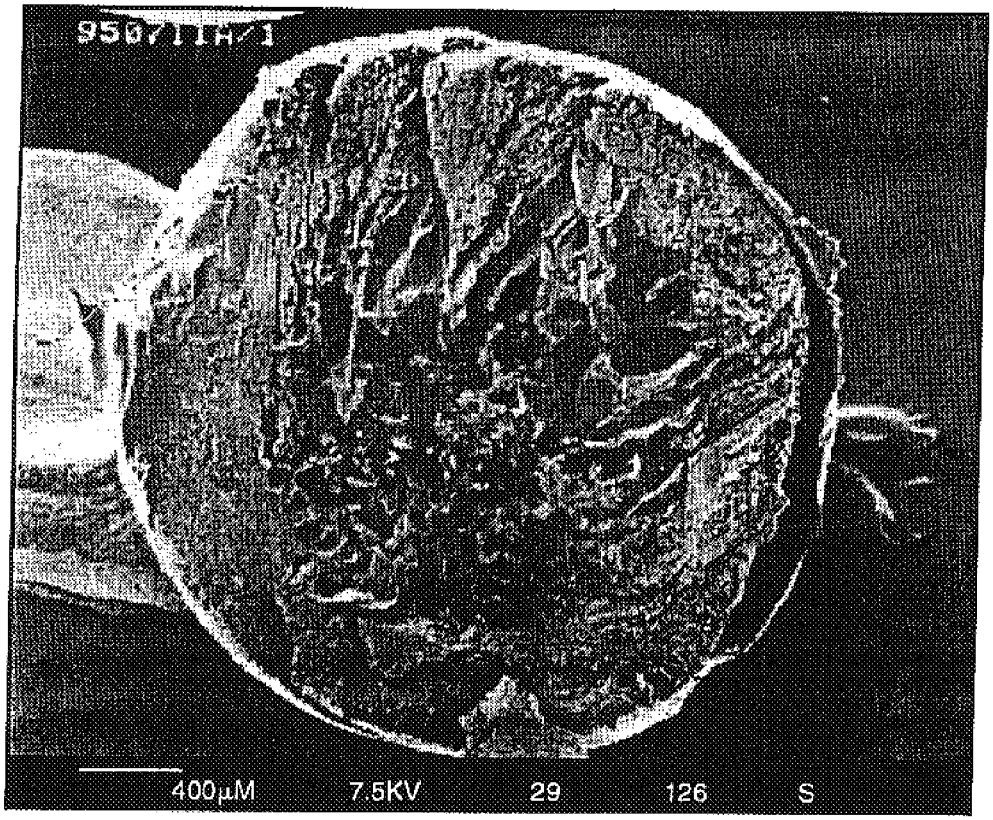
FIG. 3 shows a photomicrograph of a section through a bead obtained by a method according to the present invention, but having a thicker coating layer than the bead of FIGS. 1 and 2.

The resulting beads are sectioned and the scanning electron micrographs shown in FIGS. 1–3 are obtained. The micrographs show the porous, sponge structure of the freeze-dried core and the substantially non-porous nature of the coating over the core. It can be seen that the core has flattened pores with typical dimensions of 100 $\mu$m×100 $\mu$m×30 $\mu$m. The thickness of the non-porous coating on the beads is about 30 $\mu$m.

EXAMPLE 2

Use of the Coated Beads as a Wound Implant

Figure 4:
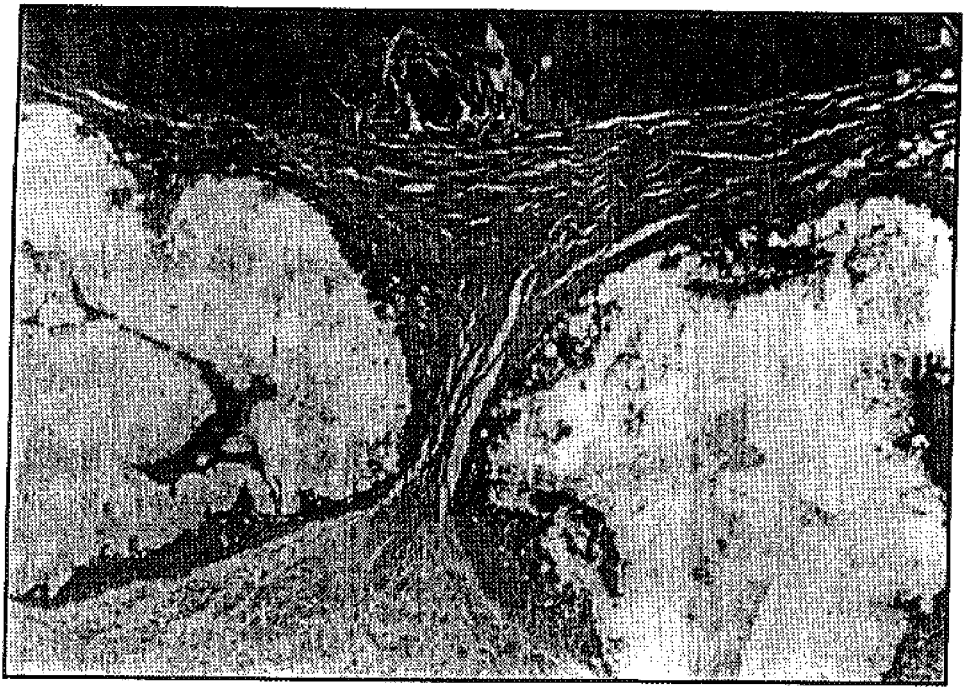
FIGS. 4 and 5 show a photomicrographs of sections through beads that have been implanted in rats.
Figure 5:
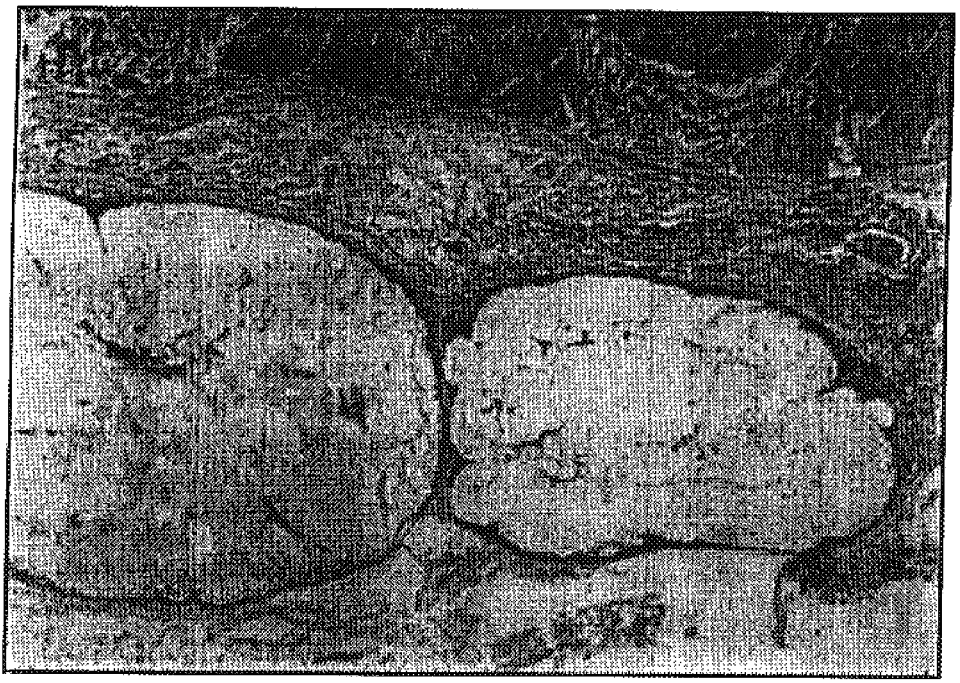

Beads produced as above are sterilised by gamma irradiation and implanted into 1×1 cm subcutaneous pockets made in the backs of rats. After 7 and 14 days the rats are sacrificed and the implanted material stabilised by placing in formalin solution. 7 μm sections are cut and stained with Massons Trichrome stain to obtain the photomicrographs of FIGS. 4 and 5. These show fibroblasts surrounding the beads, and new collagen and blood vessels are visible in the spaces between the beads.

The above embodiments have been described by way of example only. Many other embodiments of the present invention falling within the scope of the accompanying claims will be apparent to the skilled reader.

What is claimed is:

1. A material for use in a wound dressing or a wound implant, the material comprising a plurality of beads, wherein each bead comprises a porous core of a first bioabsorbable material and a substantially non-porous layer of a second bioabsorbable material around said core.

2. A material according to claim 1, wherein the first and/or the second bioabsorbable material consists essentially of collagen.

3. A material according to claim 1 or 2, wherein said beads are substantially spherical.

4. A material according to claim 1 or 2, wherein the mean outside diameter of said beads is in the range 0.1 to 4.0 mm.

5. A material according claim 4, wherein the mean thickness of said layer of said second bioabsorbable material is in the range 0.01 mm to 1.0 mm.

6. A material according to claim 5, wherein the mean pore diameter in said porous core is in the range 50 μm to 350 μm.

7. A material according to claim 6, further comprising an active therapeutic agent in said porous core and/or in said substantially non-porous layer.

8. A material according to claim 7, wherein said material is a fluid or paste comprising said beads dispersed in a liquid or gel carrier.

9. A method of making bioabsorbable beads for use in wound dressings or implants, the method comprising:

providing a dispersion of a first bioabsorbable material in a liquid solvent;

generating droplets of said dispersion;

freezing said droplets to form frozen droplets;

freeze-drying or solvent-drying the frozen droplets to form discrete porous cores of said first bioabsorbable material; and coating said porous cores with a substantially non-porous layer of a second bioabsorbable material.

10. A method according to claim 9, wherein said solvent is an aqueous solvent.

* * * * *